United States Patent [19]

Krepinsky et al.

[11] Patent Number: 5,278,303
[45] Date of Patent: Jan. 11, 1994

US005278303A

[54] POLYMER-SUPPORTED SOLUTION SYNTHESIS OF OLIGOSACCHARIDES

[75] Inventors: Jiri J. Krepinsky, Newmarket; Stephen P. Douglas, Scarborough; Dennis M. Whitfield, Toronto, all of Canada

[73] Assignee: University of Toronto Innovations Foundation, Ontario, Canada

[21] Appl. No.: 898,030

[22] Filed: Jun. 12, 1992

[51] Int. Cl.$^5$ .................. C07H 5/04; C07H 15/04; C08B 31/02; C07G 17/00

[52] U.S. Cl. .................. 536/55.3; 527/300; 527/311; 527/312; 536/49; 536/50; 536/116; 536/120; 536/124; 536/126

[58] Field of Search .................. 527/311, 300, 312; 536/49, 50, 55.3, 116, 120, 126; 530/124

[56] References Cited

U.S. PATENT DOCUMENTS

| | | | |
|---|---|---|---|
| 3,173,892 | 3/1965 | Kun | 525/153 |
| 3,941,849 | 3/1976 | Herold | 528/92 |
| 4,083,834 | 4/1978 | Komatsu et al. | 525/346 |
| 4,085,168 | 4/1975 | Milkovich et al. | 525/59 |
| 4,609,546 | 9/1986 | Hiratani | 424/78.3 |
| 4,908,405 | 3/1990 | Bayer et al. | 525/328.8 |

FOREIGN PATENT DOCUMENTS

| | | |
|---|---|---|
| 1290481 | 10/1991 | Canada . |
| 2435642 | 7/1971 | Fed. Rep. of Germany . |
| 1795353 | 4/1972 | Fed. Rep. of Germany . |
| 2077297 | 10/1971 | France . |
| 2195641 | 3/1974 | France . |
| 879950 | 10/1961 | United Kingdom . |
| 1002343 | 8/1965 | United Kingdom . |

OTHER PUBLICATIONS

Paulsen, H. *Agew. Chem. Int. Ed.* 1982, 21, 155.
Paulsen, H. *Agew. Chem. Int. Ed.* 1990, 29, 823.
Schmidt, R. R. *Agew. Chem. Int. Ed.* 1986, 25, 212.
Fugedi, P.; Garegg, P. J.; Lonn, H.; Norberg, T. *Glycoconjugate J.* 1987, vol. 4, 97.
Mootoo, D. R.; Date, V.; Fraser-Reid, B.; *J. Am. Chem. Soc.* 1988, vol. 110, 2662.
Veeneman, G. H.; Van Leeuwen, S. H.; Zuurmond, H.; Van Boom, J. H. *J. Carbohydr. Chem.* 1990, 6, 783.
Kanie, O.; Kiso, M., Hasegawa, A. *J. Carbohydr. Chem.* 1988, 7, 501.
Reddy, G. V.; Mereyala, H. B. *Tetrahedron Lett.* 1991 47, 6435.
Friesen, R. W.; Danishefsky, S. J. *J. Am. Chem. Soc.* 1989, 111, 6656.
Friesen, R. W.; Danishefsky, S. J.; *Tetrahedron* 1990, 46, 103.

(List continued on next page.)

[57] ABSTRACT

This invention relates to the preparation of oligosaccharides, using polymer supported methodology. By this method, which offers anomeric control, oligosaccharides are produced very rapidly in comparison with known methodologies. Thus, there is disclosed a process for the preparation of oligosaccharides which comprises a) forming a synthon of a saccharide and a monomethylether of polyethylene glycol or a derivative thereof, the synthon having a linkage between the oligosaccharide and the monomethylether of polyethylene glycol or a derivative thereof, which linkage can be severed under conditions that do not damage glycosidic or other bonds in a desired end product;

b) subjecting the synthon to repeated additions of a suitable glycosylating agent to form a desired oligosaccharide-polyethylene glycol linked product;

c) isolating the linked product as a solid;

d) purifying this solid; and e) releasing the oligosaccharide from the polyethylene glycol.

9 Claims, No Drawings

OTHER PUBLICATIONS

Kaur, K. J.; Alton, G.; Hindsgaul, O.; *Carbohydrate. Res.* 1991, 210, 145.

Wong, C. H.; Ichikawa, Y., Krach, T., et al., *Journal Amer. Chem. Soc.* 1991, 113, 8137.

Frechet, J. M. J.; Schuerch, C. *J. Am. Chem. Soc.* 1971, 93, 492.

Frechet, J. M. J.; Schuerch, C. *Carbohydrate Res.* 1972, 22, 399.

Mathur, N. K.; Narang, C. K.; Williams, R. E. *Polymers as Aids in Organic Chemistry;* Academic Press: N.Y., 1980 Chapter 6.

Frechet J. M. J. in *Polymer-Supported Reactions in Organic Synthesis* (Hodge, P.; Sherrington, D. C. Eds.). Wiley, Chichester 1980, p. 293 and p. 407.

Zehavi, U. *Advances in Carbohydr. Chem. Biochem.* 1988 46, 179.

Frechet, J. M. J. *Tetrahedron* 1981, 37, 663.

Bonora, G. M.; Schremin C. L.; Colonna, F. P.; Garbesi, A. *Nucl. Acids Res.* 1990, 18, 3155.

Kamaike, K.; Hasegawa, Y.; Ishido, Y. *Tetrahedron Letters* 1988, 29, 647.

Bayer, E.; Mutter, M. *Nature* 1972, 237, 512.

Bayer, E.; Mutter, M. *The Peptides* (Gross, E.; Meienhofer, J.; Eds.) Academis Press: N.Y. 1980 2, 286.

Krepinsky et al. *J. Amer. Chem. Soc.* 1991, vol. 113, No. 13; p. 5095.

*Primary Examiner*—Herbert J. Lilling
*Attorney, Agent, or Firm*—Woodcock Washburn Kurtz Mackiewicz & Norris

POLYMER-SUPPORTED SOLUTION SYNTHESIS OF OLIGOSACCHARIDES

BACKGROUND OF THE INVENTION

1. Field of the Invention

This invention relates to the preparation of oligosaccharides, using polymer supported methodology. By this method, which offers anomeric control, oligosaccharides are produced rapidly and in good yield in comparison with known methodologies.

2. Description of Related Art

Oligosaccharides may be elaborated into glycopeptides and glycolipids which have important utility in the fields of medicine, biotechnology, and related technologies. Oligosaccharides have been synthesized by solution methodologies for many years as reviewed, for example, in Paulsen, H. *Angew. Chem. Int. Ed.* (a) 1982, 21, 155; (b) 1990, 29, 823 and Schmidt, R. R. *Angew. Chem. Int. Ed.* 1986, 25, 212. These solution methodologies of oligosaccharide synthesis made dramatic advancements during the past few years described, for example, in (a) Fugedi, P.; Garegg, P. J.; Lonn, H.; Norberg, T. *Glycoconjugate J.* 1987, 4, 97; (b) Mootoo, D. R.; Date, V.; Fraser-Reid, B. *J. Am. Chem. Soc.* 1988, 110, 2662; (c) Veeneman, G. H.; Van Leeuwen, S. H.; Zuurmond, H.; Van Boom, J. H. *J. Carbohydr. Chem.* 1990, 6, 783; (d) Kanie, O.; Kiso, M., Hasegawa, A. *J. Carbohydr. Chem.* 1988, 7, 501; (e) Reddy, G. V.; Mereyala, H. B. *Tetrahedron Lett.* 1991, 47, 6435; (f) Friesen, R. W.; Danishefsky, S. J. *J. Am. Chem. Soc.* 1989, 111, 6656; (g) Friesen, R. W.; Danishefsky, S. J. *Tetrahedron* 1990, 46, 103. Still yields in the key glycosidic linkage formation steps are in the 80% range at best. In addition, certain "difficult linkages" are accessible in much lower yield, often below 50%. This reflects both the low reactivity and the instability of the reactants, in particular of the glycosylating agent. The activated glycosylating agent may decompose to several products, behaving chromatographically similar to the desired product. The excess glycosylating agent necessary to obtain an acceptable yield of coupled products often leads to reaction mixtures in which the desired compound is a relatively minor component. Thus a major obstruction to greater efficiency of glycosylation is the need for the chromatographic purification. In addition, each glycosidic linkage can form two stereoisomers (anomers) and this anomericity must be controlled. The control of anomeric specificity of glycosylation reactions performed in solutions was established in certain situations through the use of participating groups.

Methods employing enzymes for synthesis of oligosaccharides have been disclosed as well. The enzymes are either glycosyl transferases or glycosidases that normally function in the biosynthesis of oligosaccharides in living cells. The art of using enzymes for the in vitro synthesis of oligosaccharides has been described in many publications, for instance (a) Kaur, K. J; Alton, G., Hindsgaul, O., *Carbohydrate. Res.* 1991, 210, 145; (b) Wong, C. H., Ichikawa, Y., Krach, T., et al., *J. Amer Chem. Soc.* 1991, 113, 8137. Major obstacles in using the enzyme methodology are the difficulties in obtaining the pure enzymes in sufficient quantities and in purification of the final product.

Solid-state synthesis of oligosaccharides had been described in publications and reviews by (a) Frechet, J. M. J.; Schuerch, C. *J. Am. Chem. Soc.* 1971, 93, 492. (b) Frechet, J. M. J.; Schuerch, C. *Carbohydr. Res.* 1972, 22, 399; (c) Mathur, N. K.; Narang, C. K.; Williams, R. E. *Polymers as Aids in Organic Chemistry;* Academic Press: New York, 1980; Chapter 6; (d) Frechet J. M. J. in *Polymer-Supported Reactions in Organic Synthesis* (Hodge, P.; Sherrington, D. C.; Eds.); Wiley, Chichester 1980, p. 293 & p. 407; (e) Zehavi, U. *Advances in Carbohydr. Chem. Biochem.* 1988, 46, 179; (f) Frechet, J. M. J. *Tetrahedron* 1981, 37, 663. Among the problems encountered in using this methodology were: decreased glycosylation reaction rates compared to solution strategies, incomplete coupling, and lack of complete stereoselectivity. However, since two epimers (anomers) can be formed, stereochemical control is mandatory for successful synthesis of any oligosaccharide. This methodology has been considered as unsuitable for oligosaccharide synthesis because anomeric specificity could not be controlled in this reaction arrangement and the yields were low.

Polyethyleneglycol monomethylether (PEG) has been used as support for the synthesis of oligomers of peptides and nucleotides in polymer-assisted liquid synthesis as described for instance in (a) Bonora, G. M.; Scremin C. L.; Colonna, F. P.; Garbesi, A. *Nucl. Acids Res.* 1990, 18, 3155; (b) Kamaike, K; Hasegawa, Y.; Ishido, Y. *Tetrahedron Lett.* 1988, 29, 647; (c) Bayer, E.; Mutter, M. *Nature* 1972, 237, 512; (d) Bayer, E.; Mutter, M. *The Peptides* (Gross, E.; Meienhofer, J.; Eds.); Academic Press: New York 1980, 2, 286. In this reaction design the reactants are soluble in the reaction medium during the reaction itself. This methodology has not been utilized in oligosaccharide synthesis since it was considered a branch of solid-state design which has been shown to be unsuitable for the synthesis of oligosaccharides.

SUMMARY OF THE INVENTION

In contrast to the above-noted prior art, it has been discovered that syntheses of oligosaccharides can be performed efficiently and with satisfactory anomeric specificity using a polymer-supported liquid synthesis design. This approach synthesizes a polymer-carbohydrate synthon which is soluble under conditions of glycosylation, and insoluble during the work-up of the reaction mixtures. The solubility of the reactants allows the reaction kinetics and anomericity control similar to that observed in solution chemistry.

Thus the present invention provides a process for the preparation of oligosaccharides which comprises a) forming a synthon of a saccharide and a monomethylether of polyethylene glycol or a derivative thereof, the synthon having a linkage between the saccharide and the monomethylether of polyethylene glycol or a derivative thereof, which linkage can be severed under conditions that do not damage glycosidic or other linkages in a desired end product;

b) subjecting the synthon to repeated additions of a glycosylating agent to form a desired oligosaccharide-polyethylene glycol linked product;

c) isolating the linked product as a solid;

d) purifying this solid; and e) releasing the oligosaccharide from the polyethylene glycol.

The linkage formed between the monomethylether of polyethylene glycol (PEG) or a derivative thereof and the saccharide is made via a carbohydrate hydroxyl group (on the saccharide) through linkages selected from the group consisting of ester, activated ether, amide, and other similar linkages. The linkage may be formed for example by forming the ester bond from one carboxylic group of a dicarboxylic acid first either to the PEG followed by the formation of the other ester bond to a carbohydrate hydroxyl group, or vice versa. The activated ether linkage may be, for example, acetal.

The saccharide comprises at least two monosaccharide units by definition. At least one of the monosaccharides must be suitably derivatized so as to allow attachment to a monomethylether of polyethylene glycol or a derivative thereof.

The saccharide must be capable of being elaborated into a substance which is suitable for subsequent glycosylation. The resulting oligosaccharide product is preferably a linear or a branched structure usually not exceeding 10–15 monosaccharide units.

The glycosylation is performed under standard liquid-phase chemistry conditions which are well known in the art and are, of course, dependant upon the monosaccharide units, their derivatization, and their associated linkages. Monitoring of the glycosylation reaction has been found to be easily achieved through, for example, nuclear magnetic resonance, although other methods could be employed, such as chemical and/or spectroscopic means. The number of additions of glycosylating agent is determined by the amount needed for reaction completion, but it is often two or three additions. The glycosylation agent may be any saccharide or sugar in its cyclic form as long as it has an activated anomeric centre.

The monomethylether of polyethylene glycol may be selected from polymeric substances. A suitable candidate is poly(ethylene glycol) monomethylether [$HOCH_2CH_2(OCH_2CH_2)_nOCH_3$, where n is 80–160; PEG, average MW 5000]; the n may vary to 240, however, since shorter or longer chains may be necessary depending on particular properties of oligosaccharides to be synthesized. Suitable derivatives include any hydroxyl derivative or substituted hydroxyl derivatives. These substances must be capable of linkage through amide, ester, ether, or similar linkage to the carbohydrate hydroxyl groups. Suitable substituted hydroxyl derivatives include amino or thio.

The precipitation of the solid oligosaccharide-PEG bound or linked product is most effectively carried out using an anhydrous solvent. Any water present results in a reduced yield of product. An ether type solvent is preferred.

The purification of the solid oligosaccharide-PEG bound or linked product may be conducted using conventional procedures in the art. For example, recrystallization from dry ethanol or dry tetrahydrofurane is frequently used.

DESCRIPTION OF THE PREFERRED EMBODIMENTS

In one preferred form of the invention, polyethylene glycol monomethylether (PEG) may be linked to different carbohydrate hydroxyl groups through ester linkages of succinic acid (PEG-Su). When PEG-Su is bound to a carbohydrate hydroxyl, the glycosylation reaction can be driven to virtual completion by repeated additions of the glycosylating agent. Normally, use of such an excess of any glycosylating agent in the solution synthesis would create a serious problem for purification; in this procedure the non-polar fragments resulting from the decomposition of the reactants are washed off the precipitated PEG-bound product. The more polar contaminants are removed by simple recrystallization of the PEG-bound product from ethanol. Furthermore, since PEG contains a single O—$CH_3$ group ($\delta = 3.380$ ppm), the reaction course is easily monitored by NMR spectroscopy using the signal of this methyl as an internal standard.

Glycosylations of PEG-Su-bound substrates under metal an acid catalysis give good anomeric specificity when glycosylating agents are equipped with a participating group, an adjacent functional group that controls the stereochemical outcome of the reaction. Examples of such a participating group are esters.

PEG-Su has been linked to the acceptor, which is a reactant comprised of at least one monosaccharide with at least one free hydroxyl, and, due to the stereochemical control of the glycosylation by the glycosylating agent, the expected anomer is obtained. Glycosylating agents may be added several times, if required for completion of the glycosylation. After the reaction is completed, the PEG-bound product is precipitated from solution with dry diethyl ether or dry tert-butylmethyl ether, recrystallized from absolute ethanol, and after drying is ready for the next step of the synthetic sequence. PEG-Su is eventually easily cleaved from the saccharide by DBU-catalyzed methanolysis in dichloromethane or by hydrazinolysis if a phthalimido group is to be removed. Peracetylated oligosaccharides for final purification are obtained from dried residues after methanolysis by acetylation with acetic anhydride in pyridine. The expected anomer was formed in each glycosylation; the other anomer was not detected.

General procedure for handling PEG-bound reactants: After completion of the reaction, the reaction mixture is filtered to remove any solids present (e.g. molecular sieves), and concentrated to 5–10 mL per gram of PEG. PEG-saccharide is precipitated from this solution after addition of a tenfold excess of dry diethyl ether or dry tert-butylmethyl ether at 0° C. with vigorous stirring. This precipitate can be further purified by re-crystallization from absolute ethanol: the precipitate is dissolved in warm absolute ethanol (15 mL/g PEG), filtered from any solids, and after cooling, the solid product is collected, dried in vacuo, and can be used for the following step. In all other aspects the reaction conditions of reactions performed follow established protocols from classical solution chemistry. Solution chemistry protocols that may be established in the future will be applicable as well.

The following examples are used to illustrate the present invention. They should not be construed as limiting it in any way. All parts and percentages are by weight unless otherwise indicated. All abbreviations and acronyms have the standard meanings in the art. Following these examples are a set of reaction sequences using structural formulae. These formulae are identified by corresponding numerical references in the sequences and in the written description.

PREPARATION OF SYNTHON

Example 1

PEGSu-Sugar: Method I (Exemplified for the Preparation of a Compound of Structural Formula IV)

Methyl 4,6-benzylidene-2-deoxy-2-N-phthalimido-D-glucopyranoside (identified as structural formula IVa) (0.44 g, 1.07 mM), succinic anhydride (0.54 g, 5.3 mM), and DMAP (50 mg) were stirred in dry Py (50 mL) at room temperature. After completion of the reaction (monitored by TLC, ethyl acetate-hexane 2:1), Py was removed by evaporation in vacuo, and the residue subjected to flash chromatography in ethyl acetate to give 3-O-hemisuccinate (0.4 g, 70%).

The monomethylether of PEG (3.2 g; 0.8 eq.), mixed with the 3-O-hemisuccinate, was dried overnight at high vacuum over $P_2O_5$. This mixture was dissolved in anhydrous DCM (25 mL), a catalytic amount of DMAP, followed by DCC (0.16 g, 0.77 mM), was added. The solution became cloudy in 15 minutes and was stirred overnight at room temperature. The precipitated urea was removed by filtration, washed with dry DCM, and the volume of the combined filtrates was reduced to its original size. It was cooled to 0° C., anhydrous ether (250 mL) was added with vigorous stirring, and the compound of structural formula IVb precipitated out. After filtration, the solid was dissolved in hot absolute ethanol (50 mL), the solution was filtered, cooled to 4° C., and the recrystallized compound of structural formula IVb was filtered, washed with dry diethylether and dried. $^1H$ NMR($\delta$): Phth, 7.860 and 7.726 (m, 4H); PhCH=, 5.550 (s, 1H); H-1, 5.337 (d, $J_{1,2}$=8.3 Hz, 1H); sugar-OCH$_3$, 3.444 (s, 3H); PEG—OCH$_3$, 3.378 (s, 3H); Su—CH$_2$, 2.35–2.50 (m, 4H).

Example 2

PEGSu-Sugar: Method II (General Procedure)

The monomethylether of PEG (20 g) was dried overnight at high vacuum with succinic anhydride (2 g, 5 eq.) and DMAP (200 mg). To this mixture was added dry DCM (140 mL) and dry Py (30 mL). After stirring overnight, the mixture was concentrated to 75 mL, cooled to 0° C. in ice, and it was diluted with stirring to 1.0 L with cold Et$_2$O. It was allowed to stand 1 hour on ice, the solid was filtered off by suction, washed with Et$_2$O, and air-dried for 1 hour. It was further purified by recrystallization from hot absolute EtOH (700 mL) as above. $^1H$ NMR($\delta$): PEG—CH$_2$—O—Su 4.259 (brdd, 2H); PEG—OCH$_3$, 3.380 (s, 3H); Su—CH$_2$, 2.631 (m, 4H).

To a portion of this solid PEGSu (5 g) was added a monosaccharide (with 1 free OH; 1.5 eq.) and DMAP (100 mg), and the mixture was dried at high vacuum overnight. Under argon was added dry DCM (25 mL), dry CH$_3$CN (25 mL), and DCC (1.5 mL of a 1M solution in dry DCM, 1.5 eq.), and the reaction mixture was left to stir at room temperature overnight. After the work-up as in the Method I, sugar attached to PEG was obtained. The unreacted sugar was recovered from the combined filtrates.

Example 3

PEGOCH$_2$CONH Sugar: (exemplified for the preparation of 2-amino-2-deoxy glucose derivative)

The hydrochloride of 2-amino-2-deoxy-1,3,4,6-tetra-O-acetyl-D-glucopyranoside was prepared according to F. W. Dahlquist and M. A. Raftery, Biochem. 8 713 (1969) as follows: 2-Deoxy-2-acetamido-3,4,6-tri-O-acetyl-α-D-glucopyranosyl chloride (prepared by the method described by J. Conchie and G. A. Levy, Method Carbohydr. Chem. Vol. 2. (eds. R. L. Whistler and M. L. Wolfrom) Academic Press, New York (1963).) (2.0 g, 5.2 mMol) was dissolved in nitromethane (90 mL) and, 0.1M HCl (150 L) and water (150 μL) were added. After 9 days the precipitate was filtered to yield I.06 g of white crystals. Further portions of HCl and water were added to the mother liquors and the process repeated twice more to yield of another 0.8 g for a total yield of 1.86 g; (93%).

The monomethylether of PEG (10.0 g; 2 mMol) was dissolved in dry THF (200 mL), 60% NaH dispersion in mineral oil (120 mg, 3 mMol) was added and the mixture was heated to 40°–45° C. After about 1 hour t-butyl bromoacetate (0.645 mL, 4 mMol) and NaI (300 mg, 2 mMol) were added and the heating and stirring was continued overnight. The mixture was cooled to −20° C. and the precipitate was removed by filtration, rinsed with dry diethyl ether and then recrystallized from absolute ethanol as described above. The process was repeated using 5 times as much reagents (NaH, NaI and t-butyl bromoacetate) to ensure complete reaction. $^1H$ NMR($\delta$): PEG—OCH$_2$CO, 4.020 (s, 2H); (s, 3H); PEG—OCH$_3$, 3.378 (s, 3H); (CH$_3$)$_3$CO 1.476 (s, 9H). The resulting solid was dissolved in dry dichloromethane under an atmosphere of argon (30 mL) and trifluoroacetic acid (70 mL) was added. After stirring for 1 hour at room temperature, the liquids were removed in vacuo, and the residue was recrystallized from absolute ethanol to yield 9.5 g of crude solid. $^1H$ NMR($\delta$): PEG—OCH$_2$CO, 4.110 (s, 2H); (s, 3H); PEG—OCH$_3$, 3.378 (s, 3H).

The PEG derivative (5.0 g, 1 mMol) and the derivative of the glucosamine hydrochloride (0.65 g, 1.6 mMol) (both prepared as described in two above paragraphs) were dried overnight at high vacuum over $P_2O_5$. This mixture was dissolved in anhydrous DCM (50 mL) and a catalytic amount of DMAP, followed by DCC (0.23 g, 1.1 mM) were added. The solution became cloudy in 15 minutes and was stirred overnight at room temperature. The precipitated urea was removed by filtration, washed with dry DCM, and the volume of the combined filtrates was reduced to its original size. The filtrates were cooled to 0° C., anhydrous ether (500 mL) was added with vigorous stirring, and the product precipitated out. After filtration, the solid was dissolved in hot absolute ethanol (100 mL), the solution was filtered, cooled to 4° C., and the recrystallized glucosamine derivative was filtered, washed with dry diethylether and dried. $^1H$ NMR($\delta$): NH 6.188 (d $J_{NH,H2}$ 9.2, 1H); H-1, 6.197 (d, $J_{1,2}$ 3.6 Hz, 1H); H-3, 5.301 (dd $J_{3,4}$ 9.9 Hz, 1H); H-4, 5.182 (dd $J_{4,5}$ 9.6 Hz, 1H); H-6,6', 4.504 (m, 2H); PEG—OCH$_2$CO, 3.968 (m, 2H); PEG—OCH$_3$, 3.377 (s, 3H); CH$_3$CO 2.198, 2.088, 2.041, 2.024 (4×s, 3H).

Example 4

PEGOCH$_2$O-Sugar (exemplified for the preparation of 3-O-[-oxymethyl-PEG-]derivative of allyl 2-deoxy-2-acetamido-4,6-O-benzylidene-β-D-glucopyranoside)

A suspension of the monomethylether of PEG (1.35 g, 0.27 mM) in anhydrous THF (5 mL) was heated until dissolved. Sodium hydride (60% in mineral oil 0.0324 g, 0.81 mM) was added, followed, 10 minutes later, by sodium iodide (0.061 g, 0.41 mM) and chloromethyl methylsulfide (0.034 mL, 0.41 mM). After stirring at room temperature overnight, the solution was filtered through celite and the filtrate was cooled in an ice-bath. The precipitated PEG was collected by filtration, and recrystallized from absolute ethanol (20 mL) to give PEG-thiomethylmethylether (1.15 g, 84%). $^1H$ NMR($\delta$): PEG—OCH$_2$—S—CH$_3$ 4.687 (s, 2H), PE- G—OCH$_3$ 3.380 (s, 3H); PEG—O—CH$_2$—S—CH$_3$ 2.147 (s, 3H).

A stirred mixture of PEG—O—CH$_2$—S—CH$_3$ (3.56 g, 0.7 mM), allyl 2-deoxy-2-acetamido-4,6-O-benzylidene-β-D-glucopyranoside (0.98 g, 2.81 mM) and 4A molecular sieves (3 g) in dry DCM (35 mL) was treated with methyl iodide (1.1 mL) and heated in a sealed reaction vessel to 60° C. for 3 days. The reaction was cooled to 0° C. and precipitated with dry ether (25 mL) and recrystallized from hot absolute ethanol (5 mL) (repeated 2×) to give the 3-O-oxymethyl-PEG derivative of allyl 2-deoxy-2-acetamido-4,6-O-benzylidene-β-D-glucopyranoside (2.43 g, 68%). $^1$H NMR(δ): Ph 7.49, 7.45 and 7.35 (m, 5H), Ph—CH 5.560 (s, 1H), CH$_2$CH—CH$_2$— 5.9 (m, 1H).

GLYCOSYLATION

Example 5

Preparation of Trisaccharide of Structural Formula IIIb

The diol of structural formula I with attached SuPEG (312 mg, 0.057 mM) was mixed with bromide II (56 mg, 2 eq.), AgOTf (28 mg, 2 eq.), DBMP (11 mg, 1 eq.), and a small portion of powdered 4A molecular sieves, and the mixture was dried at high vacuum overnight. Then the flask was cooled in ice water under argon, DCM (4 mL) was added and the reaction mixture was stirred for two hours. At this point another portion of dried bromide of structural formula II (2 eq.), AgOTf (2 eq.), and DBMP (1 eq.), were added, and an identical addition was made after another 2 hours. The stirring was continued overnight, the reaction mixture was diluted with dry DCM (10 mL) and the molecular sieves and precipitated silver salts were filtered off. The filtrate was evaporated to dryness, the residue was redissolved in dry DCM (4 mL), the solution was cooled to 0° C. in an ice bath, and the product was precipitated by the addition of Et$_2$O (40 mL) with vigorous stirring. After standing for 1 hour, the precipitate was collected by filtration, washed with Et$_2$O, and dried in air for at least 1 hour. The dry solid was dissolved in warm absolute ethanol (15 mL), filtered from undissolved solids, and the solution was allowed to crystallize at 4° C. The solid was collected by filtration, washed with cold absolute EtOH and dry Et$_2$O, and dried in vacuo to give trisaccharide attached to SuPEG denoted by structural formula IIIb. $^1$H NMR(δ): Phth, 7.860 (m, 4H) & 7.75 (m, 4H); Gal H-1, 4.30 (1H); GlcNPhth(β1-6) H-1, 5.425 (d, J$_{1,2}$=8.5 Hz, 1H); GlcNPhth(β1-4) H-1, 5.462 (d, J$_{1,2}$=8.5 Hz, 1H); Bz$_o$, 7.999 (brd, 2H); Bz$_m$, 7.416 (brt, 2H); Bz$_p$ 7.564 (brt, 1H).

Example 6

Preparation of Disaccharide of Structural Formula IIIa

The diol of structural formula I with attached SuPEG (153 mg, 0.057 mM) was mixed with bromide of structural formula II (1.1 eq.), Ag$_2$CO$_3$ (7 eq.), and a small portion of powdered 4A molecular sieves, and the mixture was dried at high vacuum overnight. Then the flask was cooled in ice water under argon, dry DCM (2 mL) was added, and the reaction mixture was allowed to warm up slowly to room temperature and stirring was continued for 2 days. The reaction mixture was worked up as described for the compound of structural formula IIIb. $^1$H NMR(δ): Gal H-1, 4.447 (d, J$_{1,2}$=8.0 Hz, 1H); GlcNPhth H-1, 5.425 (d, J$_{1,2}$=8.5 Hz, 1H); 3xCH$_3$COO, 2.117, 2.033, 1.866 (3s, 9H).

Example 7

Preparation of disaccharide of structural formula VI

To a cold solution (−10° C.) of the saccharide with attached SuPEG (structural formula IV, 77 mg, 0.013 mM) and imidate of structural formula V (0.02 g, 0.04 mMol) in dry DCM (1 mL), BF$_3$.Et$_2$O (0.08M in DCM, 6 μl, 0.048 mM) was added. The reaction mixture was allowed to warm up slowly to room temperature and stirring was continued overnight. The reaction mixture was worked up as described for the compound of structural formula IIIb. This procedure was repeated two more times, and complete galactosylation gave the compound of structural formula VI. $^1$H NMR(δ): Phth, 7.771 and 7.423 (m, 4H); GlcNPhth H-1, 5.231 (d, J$_{1,2}$=8.4 Hz, 1H); Gal H-1, 4.898 (d, J$_{1,2}$=8.1 Hz, 1H); GlcNPhth-OCH$_3$, 3.438 (s, 3H); PEG—OCH$_3$, 3.380 (s, 3H); Su—CH$_2$, 2.4–2.6 (m, 4H); 4xCH$_3$COO, 2.132, 2.086, 1.984, 1.822 (4s, 12H).

Example 8

Oligosaccharide cleavage from the polymer followed by acetylation: Cleavage of trisaccharide of structural formula IIIb The trisaccharide moiety was removed from the polymer in structural formula IIIb (330 mg) by treatment with N$_2$H$_4$.H$_2$O (1 mL) and EtOH (2 mL) at 70° C. for 2 hours. The liquids were removed by co-evaporation with toluene (2×10 mL) and the resulting solid was dried at high vacuum for 2 h, cooled on ice, and dry Py (2 mL) and Ac$_2$O (1 mL) were added under argon and the reaction mixture was stirred overnight at room temperature. The liquids were removed at oil pump vacuum, the residue was dissolved in hot absolute EtOH (15 mL), filtered, and allowed to precipitate at 4° C. The precipitated PEG was filtered off, rinsed with cold absolute EtOH, the combined filtrate and washings were evaporated to dryness and purified by chromatography on silica gel (DCM:MeOH 40:1, followed by 10:1) to yield peracetylated trisaccharide. $^1$H NMR(δ): GlcNAc(β1-6) H-1, 4.28; GlcNAc(β1-4) H-1, 4.690 (d, J$_{1,2}$=8.4 Hz, 1H); Gal H-1, 4.387 (d, J$_{1,2}$ 8.0 Hz, 1H). Exact mass (note the presence of Galβ1-OCD$_3$) for C$_{39}$H$_{54}$O$_{24}$N$_2$D$_3$ MH$^+$: calc. 940.3489; found 940.3474.

Example 9

Oligosaccharide cleavage from the polymer followed by acetylation: Cleavage of disaccharide of structural formula IIIa The disaccharide moiety was removed from the polymer by overnight treatment of the compound of structural formula IIIa (290 mg) dissolved in dry DCM (2 mL) and dry MeOH (0.5 mL) with DBU (1 drop) with stirring. The PEG and deprotected sugar were precipitated with dry Et$_2$O as above, and removed by filtration. The precipitate containing PEG and oligosaccharide was dissolved in hot absolute EtOH (10 mL), the PEG was allowed to crystallize out, filtered and washed with cold absolute EtOH. The combined filtrate and washings were evaporated to dryness, and the residue was treated with dry Py (2 mL) and Ac$_2$O (1 mL) at room temperature overnight as above. The liquids were removed by co-evaporation with toluene and the residue was purified by chromatography on silica gel to yield a peracetylated N-phthalimido disaccharide. $^1$H NMR($\delta$): GlcNPhth H-1, 5.435 (d, $J_{1,2}=8.6$ Hz, 1H); Gal H-1, 4.250 (d, $J_{1,2}=7.9$ Hz, 1H); Phth, 7.838 (m, 2H) and 7.730 (m, 2h). Exact mass (note the presence of Gal 1-OCD$_3$) for $C_{32}H_{36}O_{17}ND_3$ MH$^+$: calc. 706.1983; found 706.1983.

A separate sample treated with hydrazine hydrate and acetylated as in the compound of structural formula IIIb gave the known peracetylated disaccharide. This method is described in the literature, in particular in Whitfield, D. M.; Ruzicka, C. J.; Carver, J. P.; Krepinsky, J. J. Can. J. Chem. 1987, 65, 693.

Example 10

The oligosaccharide products of Example 3 can be released from PEG by treatment with hydrazine hydrate in ethanol (1:2, v/v) at 70° C. The oligosaccharide products of Example 4 can be released from PEG by treatment with 60% acetic acid at 100° C.

Explanations

The following structural formulae and reaction schemes illustrate some of the examples, as already noted. The numbers which appear above the arrows relate to the reaction conditions and reagents required in the various steps. The following is a description of these conditions and reagents with the numbers corresponding to those in the illustrated schemes.

1. AgOTf, DBMP, CH$_2$Cl$_2$, 4A ms, 91%
2. Ag$_2$CO$_3$, DBMP, CH$_2$Cl$_2$, 4A ms, 75%
3. BF$_3$.Et$_2$O, DBMP, CH$_2$Cl$_2$, 70%
4. succinic anhydride, DMAP, pyridine 70%
5. PEG, DCC, DMAP, CH$_3$CN, 90%
6. 60% aqueous AcOH, 100° C., 85%
7. PEG, DCC, DMAP, CH$_2$Cl$_2$, 93%
8. TBDPS Cl, imidazole, CH$_2$Cl$_2$, 94%
9. 60% aqueous AcOH, 60° C., 91%

Alternatively, the appropriate hydroxyl can be esterified by PEG-hemisuccinate using DCC activation with DMAP.

ABBREVIATIONS py = pyridine
Ac = acetyl
AgOTf = CF$_3$SO$_3$Ag
Bz = benzoyl
DBMP = 2,6-di-tert-butyl-4-methylpyridine
DBU = 1,8-diazabicyclo[5.4.0]undec-7-ene
DCM = dichloromethane
DCC = 1,3-dicyclohexylcarbodiimide
DMAP = 4-(dimethylamino)pyridine
4A ms = 4A molecular sieves
PEG = —OCH$_2$CH$_2$(OCH$_2$CH$_2$)$_n$OCH$_3$, n=110
Phth = phthalimido
Su = COCH$_2$CH$_2$CO—
Su—PEG = —COCH$_2$CH$_2$COOCH$_2$CH$_2$(OCH$_2$CH$_2$)$_n$OCH$_3$, n=180-240
TBDPS = tert-butyldiphenylsilyl

REACTION SCHEMES
ILLUSTRATING GLYCOSYLATIONS

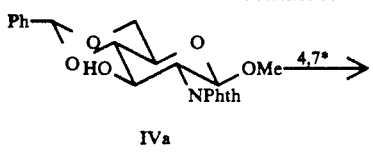
IVa

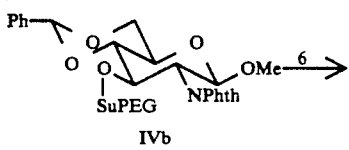
IVb

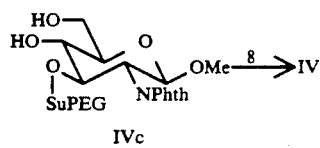
IVc

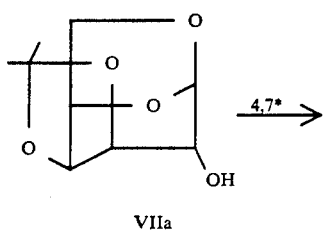
VIIa

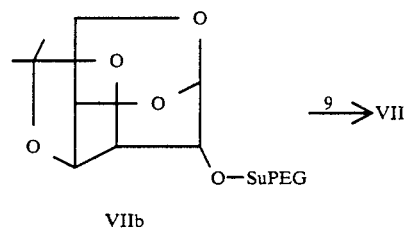
VIIb

We claim:
1. A process for the preparation of oligosaccharides which comprises:
   a) reacting a first reactant saccharide having at least one monosaccharide unit with a second reactant which is a polyethylene glycol monomethyl ether, the two reactants being linked through an ester linkage of dicarboxylic acid bound to a carbohydrate carboxyl;
   b) subjecting the saccharide-polyethylene glycol monomethyl ether reaction product to a glycosylation reaction through a plurality of additions of a glycosylation agent having an activated anomeric center, while monitoring the reaction for completion;
   c) isolating the polyethylene glycol-oligosaccharide as a solid;
   d) purifying the solid; and
   e) releasing the oligosaccharide from the polyethylene glycol.
2. The method of claim 1 wherein said dicarboxylic acid is succinic acid.
3. The method of claim 1 wherein said isolating step comprises precipitation in the presence of an anhydrous solvent.
4. The method of claim 3 wherein said solvent is anhydrous ether.
5. The method of claim 1 wherein said purification step comprises recrystallization.
6. The method of claim 1 wherein the monitoring step employs magnetic resonance spectroscopy.
7. The method of claim 1 wherein said releasing step comprises hydrolysis.
8. The method of claim 1 wherein the polyethylene glycol has a molecular weight of about 5000.
9. A process as claimed in claim 1 wherein the dicarboxylate group from succinic acid is attached to the polyethylene glycol monomethylether and to a hydroxy group of the oligosaccharide.

* * * * *